United States Patent [19]
Vacanti et al.

[11] Patent Number: 5,804,178
[45] Date of Patent: Sep. 8, 1998

[54] IMPLANTATION OF CELL-MATRIX STRUCTURE ADJACENT MESENTERY, OMENTUM OR PERITONEUM TISSUE

[75] Inventors: Joseph P. Vacanti, Winchester; Robert S. Langer, Newton; Lynt Johnson, Randolph, all of Mass.

[73] Assignees: Massachusetts Institute of Technology, Cambridge; Children's Medical Center Corporation, Boston, both of Mass.

[21] Appl. No.: 203,509

[22] Filed: Feb. 28, 1994

Related U.S. Application Data

[63] Continuation of Ser. No. 680,608, Apr. 1, 1991, abandoned, which is a continuation of Ser. No. 343,158, Apr. 25, 1989, abandoned, which is a continuation of Ser. No. 123,579, Nov. 20, 1987, abandoned, which is a continuation-in-part of Ser. No. 933,018, Nov. 20, 1986, abandoned.

[51] Int. Cl.$^6$ .............................. C12N 11/08; C12N 5/00; A61F 2/28; A61F 2/18
[52] U.S. Cl. .................. 424/93.7; 424/422; 424/426; 424/486; 424/548; 424/549; 435/177; 435/178; 435/180; 435/181; 435/395; 435/398; 435/402
[58] Field of Search ................................. 435/177, 178, 435/180, 182, 181, 240.1, 240.23, 240, 242, 243, 395, 398, 402; 424/93.7, 422, 423, 426, 486, 548, 549; 436/823; 524/24; 525/421; 623/11, 12, 13

[56] References Cited

U.S. PATENT DOCUMENTS

| | | | |
|---|---|---|---|
| 2,609,347 | 9/1952 | Wilson | 260/2.5 |
| 2,653,917 | 9/1953 | Hammon | 260/2.5 |
| 2,659,935 | 11/1953 | Hammon | 18/55 |
| 2,664,366 | 12/1953 | Wilson | 117/138.8 |
| 2,664,367 | 12/1953 | Wilson | 117/138.8 |
| 2,846,407 | 8/1958 | Wilson | 260/2.5 |
| 3,826,241 | 7/1974 | Bucalo | 128/1 R |
| 3,880,991 | 4/1975 | Yolles | 424/22 |
| 3,949,073 | 4/1976 | Daniels | 424/177 |
| 3,960,150 | 6/1976 | Hussain et al. | 128/260 |
| 3,974,526 | 8/1976 | Dardik et al. | 3/1.4 |
| 3,982,725 | 9/1976 | Homsy | 3/1 |
| 3,992,725 | 11/1976 | Homsy | 633/4 |
| 4,026,304 | 5/1977 | Levy | 128/419 |
| 4,060,081 | 11/1977 | Yannas | 128/156 |
| 4,069,307 | 1/1978 | Higuchi et al. | 424/22 |
| 4,137,921 | 2/1979 | Okuzumi | 428/335.5 |
| 4,141,087 | 2/1979 | Shalaby et al. | 3/1 |
| 4,144,126 | 3/1979 | Burbidge | 195/1.1 |
| 4,186,448 | 2/1980 | Brekke | 3/1.9 |
| 4,192,827 | 3/1980 | Mueller et al. | 525/123 |
| 4,205,399 | 6/1980 | Shalaby et al. | 3/1 |
| 4,228,243 | 10/1980 | Iizuka | 435/285 |

(List continued on next page.)

FOREIGN PATENT DOCUMENTS

| | | |
|---|---|---|
| 0226061 | 6/1987 | European Pat. Off. . |
| 0282746 | 9/1988 | European Pat. Off. . |
| 0339607 | 11/1989 | European Pat. Off. . |
| 2853614 | 7/1979 | Germany . |
| 62-011 459 | 1/1987 | Japan . |
| 63-196 273 | 2/1987 | Japan . |
| 63-074 498 | 4/1988 | Japan . |
| 63-196 595 | 8/1988 | Japan . |
| WO 87/06120 | 10/1987 | WIPO . |
| WO 89/00413 | 1/1989 | WIPO . |

OTHER PUBLICATIONS

Yannas, et al., *Science* 215, 174–176 (1982).
Yannas, et al., *Polym. Prepr. Am. Chem. Soc. Div. Polym. Chem.* 16(2), 209–214 (1975).
Yannas, et al., *J. Biomen. Mater. Res.* 14, 65–81 (1980).
Jaksie, et al., *Ann. Rev. Med.* 38, 107 (1987).
Burke, *The Role of Extracellular Matrix in Development* 351–355 (Alan R. Liss, Inc., NY 1984).
Yannas, et al., *Iss. Polym. Biomaterial* 106, 221–230 (1986).
Yannas, *J. of Trauma* 24(9), S29–S39 (1984).
Yannas, et al., *Polym. Sci. Technol. Iss. Adv. Biomed. Polymer* 35, 1–9 (Plenum 1987).
Yannas, et al., *Polym. Material Sci. Eng.* 53, 216–218 (1985).
Cosimi, et al., *Surgical Clinics of N.A.* 58(2), 435–451 (1978).
Jones, et al., *Cancer Invasion and Metastasis: Biologic and Therapeutic Aspects* pp. 177–185 (Raven Press, NY 1984).
Schubert, et al., *J. Cell. Biol.* 104, 635–643 (1987).
Bazeed et al., *Urology* 21(5), 501–504 (1983).
Mounzer et al., *Urology* 28(2), 127–130 (1986).
Bazeed et al., *Urology* 21(1), 53–57 (1983).
Kusano, et al., *Acta Japoni Hepato* 63, 345–351 (1089).
Alberts, et al., *Molecular Biology of the Cell*, 893 and 894 (1983).

(List continued on next page.)

Primary Examiner—David M. Naff
Attorney, Agent, or Firm—Arnall Golden & Gregory, LLP

[57] ABSTRACT

A matrix structure containing attached cells such as endocrine cells, fibroblasts, endothelial cells or genitourinary cells is implanted in a patient adjacent tissue having a high surface area and vasculature such as mesentery, omentum or peritoneum tissue. Large volumes of cells can be attached to the matrix and the matrix implanted with minimum trauma and blood loss into a patient to produce a functional organ equivalent. Multiple matrix structures containing cells can be implanted to functionally resemble naturally occurring organs. Implanting multiple matrices between folds of the mesentery is particularly well suited for growth of endocrine structures, including liver, pancreas, and adrenal gland. The matrix structure is preferably formed from a biodegradable artificial polymer. Collagen and non-biodegradable materials can also be used, and the matrix structure can be overlaid with a material that enhances cell attachment. Materials such as angiogenesis factors can be incorporated into a matrix and implanted prior to implanting the matrix containing cells or the materials can be incorporated into the matrix containing cells. Cells attached to the matrix may be cultured in vitro prior to implanting. Matrix structures containing different types of cells can be implanted juxtapositioned with each other.

14 Claims, 4 Drawing Sheets

U.S. PATENT DOCUMENTS

| | | | |
|---|---|---|---|
| 4,239,664 | 12/1980 | Teng et al. | 260/17.4 R |
| 4,243,775 | 1/1981 | Rosensaft et al. | 525/415 |
| 4,277,582 | 7/1981 | Mueller et al. | 525/421 |
| 4,280,954 | 7/1981 | Yannas et al. | 260/123.7 |
| 4,304,591 | 12/1981 | Mueller et al. | 71/93 |
| 4,304,866 | 12/1981 | Green et al. | 435/240.23 |
| 4,328,204 | 5/1982 | Wasserman | 424/486 |
| 4,347,847 | 9/1982 | Usher | 128/334 |
| 4,348,329 | 9/1982 | Chapman | 260/403 |
| 4,352,883 | 10/1982 | Lim et al. | 435/178 |
| 4,356,261 | 10/1982 | Kuettner | 435/68 |
| 4,391,797 | 7/1983 | Folkman et al. | 424/19 |
| 4,427,808 | 1/1984 | Stol et al. | 524/24 |
| 4,431,428 | 2/1984 | Schmer | 604/897 |
| 4,438,198 | 3/1984 | Schmer | 435/178 |
| 4,439,152 | 3/1984 | Small | 433/173 |
| 4,440,921 | 4/1984 | Allcock et al. | 528/168 |
| 4,444,887 | 4/1984 | Hoffmann | 435/240 |
| 4,446,234 | 5/1984 | Russo et al. | 435/29 |
| 4,450,150 | 5/1984 | Sidman | 424/1.1 |
| 4,456,687 | 6/1984 | Green | 435/240.25 |
| 4,458,678 | 7/1984 | Yannas et al. | 128/155 |
| 4,485,096 | 11/1984 | Bell | 424/95 |
| 4,485,097 | 11/1984 | Bell | 424/95 |
| 4,489,056 | 12/1984 | Himmelstein | 424/22 |
| 4,495,174 | 1/1985 | Allcock et al. | 424/78 |
| 4,505,266 | 3/1985 | Yannas et al. | 128/1 R |
| 4,520,821 | 6/1985 | Schmidt | 435/240.21 |
| 4,528,265 | 7/1985 | Becker | 435/172.1 |
| 4,544,516 | 10/1985 | Hughes et al. | 264/108 |
| 4,545,082 | 10/1985 | Hood | 623/12 |
| 4,546,500 | 10/1985 | Bell | 623/1 |
| 4,559,304 | 12/1985 | Kasai et al. | 435/240.43 |
| 4,563,350 | 1/1986 | Nathan et al. | 424/95 |
| 4,563,489 | 1/1986 | Urist | 524/21 |
| 4,563,490 | 1/1986 | Stol et al. | 524/24 |
| 4,576,608 | 3/1986 | Honsy | 623/12 |
| 4,609,551 | 9/1986 | Caplan et al. | 424/95 |
| 4,637,931 | 1/1987 | Schmitz | 424/78 |
| 4,642,120 | 2/1987 | Nevo et al. | 623/16 |
| 4,645,669 | 2/1987 | Reid | 424/95 |
| 4,675,189 | 6/1987 | Kent et al. | 424/490 |
| 4,681,763 | 7/1987 | Nathanson et al. | 424/95 |
| 4,713,070 | 12/1987 | Mano | 623/12 |
| 4,757,017 | 7/1988 | Cheung | 435/240.23 |
| 4,757,128 | 7/1988 | Domb | 528/271 |
| 4,778,749 | 10/1988 | Vasington et al. | 435/2 |
| 4,846,835 | 7/1989 | Grande | 623/11 |
| 4,853,324 | 8/1989 | Viles | 435/2 |
| 4,868,121 | 9/1989 | Scharp et al. | 435/268 |
| 4,880,622 | 11/1989 | Allcock et al. | 424/28 |
| 4,888,176 | 12/1989 | Larger et al. | 424/426 |
| 4,891,225 | 1/1990 | Langer et al. | 424/428 |
| 5,041,138 | 8/1991 | Vacant et al. | 623/16 |

OTHER PUBLICATIONS

Allcock, et al., "Synthesis of Poly(amino acid alkyl ester) phosphazenes," Macromolecules 10:824–830 (1977).

Allcock, H.R., et al., "Phosponitrillic Compounds. XV. High Molecular Weight Poly[bis(amino)phosphazenes] and Mixed–Substituent Poly(aminophosphazenes)," Inorg. Chem. 11(11), 2584–2590 (1972).

Allcock, et al., "Synthesis of Sugar–Substituted Cyclic and Polymeric Phosphazenes and Their Oxidation, Reduction, and Acetylation Reactions," Macromolecules 16(4), 715 (Apr. 1983).

Allcock, et al., "Polyphosphazenes with Etheric Side Groups: Prospective Biomedical and Solid Electrolyte Polymers," Macromolecules 19(1), 1508 (Jan. 1986).

Allcock, et al., "Amphiphilic polyphosphazenes as membrane materials: influence of side group on radiation cross–linking," Biomaterials, 9(6), 500–508 (Nov. 1988).

Allcock, et al., "Glyceryl Polyphosphazenes: Synthesis, Properties, and Hydrolysis," Macromolecules 21(7), pp. 1980–1985 (1988).

Allcock, et al., "Hydrolysis Pathways for Aminophosphazenes," Inorg. Chem. 21(1), 515–521 (Jan. 1982).

Allcock, et al., "An Ionically Cross–Linkable Polyphosphazene: Poly[bis(carboxylatophenoxy)phosphazene] and Its Hydrogels and Membranes," Macromolecules 22(1), 75 (Jan. 1989).

Anderson, David J., et al., Caltech Biology (1987).

Anderson, Kathryn D., et al., "Gene Expression in Implanted Rat Hepatocytes Following Retroviral–Mediated Gene Transfer," Somatic Cell and Molecular Genetics, vol. 15, pp. 215–227 (1989).

Backlund, Erik–Olof, et al., "Toward a Transplantation Therapy in Parkinson's Disease," Annals of the N.Y. Academy of Science, vol. 495, pp. 658–673 (1987).

Stemple, Derek L., "A Factor that Induces Adrenergic Differentiation in Avian Neural Creat Cells," Caltech Biology (1987).

Sullivan, Walter, "Spinal Injury Research Yields a Glimmer of Hope," The New York Times, (Jul. 14, 1987).

Tavassoli, Mehdi, et al., "Studies on Regeneration of Heterotopic Spienic Autotransplants," Blood, vol. 41, No. 5, pp. 701–709 (May 1973).

Thompson, John A., et al., "Heparin–Binding Growth Factor 1 Induces the Formation of Organoid Neovascular Structures In Vivo," Proc. Natl. Acad. Sci. U.S.A., vol. 86, pp. 7928–7932 (Oct. 1989).

Thompson, J.A., et al., "Implantable Bioreactors: Modern Concepts of Gene Therapy," Current Communications in Molecular Biology: Therapeutic Peptides and Proteins, D. Marshak, ed., pp. 143–147 (Cold Spring Harbor Laboratory 1989).

Tomomura, Akito, et al., "The Control of DNA Synthesis in Primary Cultures of Hepatocytes From Adult and Young Rats: Interactions of Extracellular Matrix Components, Epidermal Growth Factor, and the Cell Cycle," J. Cellular Physiology, vol. 130, No. 1, pp. 221–227 (1987).

Unipoint Industries, Inc., "Polyvinyl Alcohol Foam for Surgical and Industrial Use" (May 1983).

Vargo, Rita, et al., "Infection as a Complication of Liver Transplant," Critical Care Nurse, vol. 9, No. 4, pp. 52–62 (Apr. 1989).

Viig, J., et al., "UV–Induced DNA Excision Repair in Rat Fibroblasts During Immortalization and Terminal Differentiation In Vitro," Exp. Cell Res. 167 (Dec. 1986) 517–530.

Rosen, Howard B., et al., "Bioerodible Polymers for Controlled Release Systems," Controlled Release Systems: Fabrication Technology, vol. 11, Chapter 5, pp. 83–110 (1983).

Rosen, Howard B., et al., "Bloerodible Polyanhydrides for Controlled Drug Delivery," Butterworth & Co. (Publishers) Ltd. (1983).

Sawada, N., et al., "Effects of Extracellular Matrix Components of the Growth and Differentiation of Cultured Rat Hepatocytes," In Vitro Cellular & Development Biology, vol. 23, No. 4, pp. 267–273 (Apr. 1987).

Schmeck, Harold M., "Doctors Try to Capitalize on the Liver's Ability to Regenerate Itself," The New York Times Medical Science (May 16, 1989).

Seckel, B.R., et al., "Nerve Regeneration Through Synthetic Biodegradable Nerve Guides: Regulation by the Target Organ," *Plast. Reconstr. Surg.*, 74(2):173–81 (Aug. 1974).

Shine, H.D., et al., "Cultured Peripheral Nervous System Cells Support Peripheral Nerve Regeneration Through Tubes in the Absence of Distal Nerve Stump," *J. Neuroscience Res.*, 14(4):393–401 (1985).

Siegel, Ronald A., et al., "Controlled Release of Polypeptides and Other Macromolecules," *Pharmaceutical Research 1984*, pp. 2–10.

Sirica, Alphonse, et al., "Fetal Phenotypic Expression by Adult Rat Hepatocytes on Collagen Gel/Nylon Meshes," *Proc. National Academy Science USA*, vol. 76, No. 1, pp. 283–287 (Jan. 1979).

Sirica, Alphonse, et al., "Use of Primary Cultures of Adult Rat Hepatocytes on Collagen Gel–Nylon Mesh to Evaluate Carcinogen–Induced Unscheduled DNA Synthesis," *Cancer Research*, 40, 3259–3267 (Sep. 1980).

Sladek, J.R., Jr., et al., "Reversal of Parkinsonism by Fetal Nerve Cell Transplants in Primate Brain," *Annals of the New York Academy of Sciences*, vol. 495, pp. 641–657 (New York 1987).

Sladek, J.R., Jr., et al., "Survival and Growth of Fetal Catecholamine Neurons Transplanted into Primate Brain," *Brain Res. Bull.*, 17(6):809–18 (Dec. 1986).

Sladek, John R., Jr., et al., "Neural Transplantation: A Call for Patience Rather Than Patients," *Science*, vol. 240, pp. 386–388 (Jun. 10, 1988).

Sladek, John R., Jr., et al., "Transplantation of Fetal Dopamine Neurons in Primate Brain Reverses MPTP Induced Parkinsonism," *Progress in Brain Research*, vol. 71, pp. 309–323 (1987).

Notter, M.F., et al., "Neuronal Properties of Monkey Adrenal Medulla In Vitro," *Cell Tissue Res.*, 244(1):69–76 (1986).

Nyilas E., et al., "Peripheral Nerve Repair with Bioresorbable Prosthesis," *Trans. Am. Soc. Artif. Intern. Organs*, 29:307–13 (1983).

Oellrich, R.G., et al., "Biliary Atresia," *Neonatal Network*, pp. 25–30 (Apr. 1987).

Oliwenstein, Lori, "The Power of Plastics," *Discover*, p. 18 (Dec. 1989).

Omery, Anna, et al., "A Nursing Perspective of the Ethical Issues Surrounding Liver Transplantation," *Heart & Lung*, vol. 17, No. 6 (Nov. 1988).

Pasik, P., *Annals of the N.Y. Academy of Science*, vol. 495, pp. 674–675 (1987).

Patterson, P.H., et al., "Adrenal Chromaffin Cell–Derived Cholinergic Neurons for Brain Transplants," *Caltech Biology* (1987).

Patterson, P.H., et al., *Caltech Biology*, pp. 199–200 (1987).

Perlow, M.J., "Brain Grafting as a Treatment for Parkinson's Disease," *Neurosurgery*, vol. 20, No. 2, pp. 335–342 (1987).

Ptasinska–Urbanska, et al., "Intrascleral Introduction of Isolated Allogeneic Chondrocytes Capable of Cartilage Reformation in Rabbits; Possible Procedure in Treatment of Detachment of the Retina," *Exp. Eye Res.*, vol. 24, No. 3, pp. 241–247 (1977).

Redmond, D.E., Jr., et al., "Fetal Neuronal Grafts in Monkeys Given Methyphenyltetrahydropyridine," *The Lancet*, pp. 1125–1127 (May 17, 1986).

Redmond, D.E., Jr., et al., "Transplants of Primate Neurons," *Lancet*, 2(8514):1046 (Nov. 1, 1986).

Reid, L.M., et al., "Long–Term Cultures of Normal Ray Hepatocytes on Liver Biomatrix," *Ann. NY Acad. Sci.* (1980).

Rhine, et al., "Polymers for Sustained Macromolecule Release: Procedures to Fabricate Reproducible Delivery Systems and Control Release Kinetics," *Journal of Pharmaceutical Sciences*, vol. 69, No. 3 (Mar. 1980).

Madison, R., et al., "Nontoxic Nerve Guide Tubes Support Neovascular Growth in Transected Rat Optic Nerve," *Exp Neurol*, 86(3):448–61 (Dec. 1984).

Madison, R., et al., "Peripheral Nerve Regeneration With Entubulation Repair: Comparison of Biodegradeable Nerve Guides Versus Polyethylene Tubes and the Effects of a Laminin–Containing Gel," *Exp Neurol*, 95(2):387–90 (Feb. 1987).

Marciano, F.F., et al., "Structural and Functional Relationships of Grafted Vasopressin Neurons," *Brain Res.*, 370(2):338–42 (Apr. 9, 1986).

Mesnil, et al., "Cell Contact but Not Junctional Communication (Dye Coupling) with Biliary Epithelial Cells is Required for Hepatocytes to Maintain Differentiated Functions," *Exper. Cell Res.*, 173 (1987) 524–533.

Michalopoulos, G., et al., "Primary Culture of Parenchymal Liver cells on Collagen Membranes," *Exper. Cell. Res.* 94 (1975) 70–78.

Millaruelo, Ana I., "Role of Plasminogen Activator and its Inhibitors in Axonal Outgrowth and Regeneration In Vivo," *Caltech Biology*, (1987).

Mooney, David, et al., "Control of Hepatocyte Function Through Polymer–Substrate Modulation," Thesis Proposal—Department of Chemical Engineering, Massachusetts Institute of Technology (Sep. 22, 1989).

Mooney, David, et al., "Switching from Differentiation to Growth in Hepatocytes: Control by Extracellular Matrix," *J. Cell Biology*, V. 111, No. 5, p. 149a (Nov. 1990).

Movitz, David, "Accessory Spleens and Experimental Splenosis Principles of Growth," *The Chicago Medical School Quarterly*, vol. 26, No. 4, pp. 183–187 (Winter–Spring 1967).

Nastelin, Jennifer Green, "Pancreatic Islet Cell Transplantation: Optimization of Islet Cell Adhesion by Altering Polymer Surface Characteristics," Harvard–M.I.T. Division of Health Sciences and Technology (Feb. 1990).

Naughton, B.A., et al., "Granulopoiesis and Colony Stimulating Factor Production in Regenerating Liver," *Exp. Hematol.*, vol. 10, No. 5, pp. 451–458 (May 1982).

Naughton, B.A., et al., "Long–Term Growth of Rat Bone Marrow Cells in a Three–Dimensional Matrix," *The Anatomical Record*, vol. 18, No. 1, p. 97A (May 1987).

Naughton, G.K., et al., "Erythropoietin Production by Macrophages in the Regenerating Liver," *Journal of Surgical Oncology*, vol. 30, pp. 184–197 (1985).

Ingber, et al., "Control of Capillary Morphogenesis: A Molecular System of Mechanical Switches," *J. Cell Biol.*, 107:797a (1988).

Ingber, et al., "Growth Control through Fibronectin–Dependent Modulation of Cell Shape," *J. Cell Biol.*, 105:219a (1987).

Ingber, et al., "How Does Extracellular Matrix Control Capillary Morphogenesis?", *Cell*, vol. 58, pp. 803–805 (Sep. 8, 1989).

Ingber, et al., "Mechanochemical Switching Between Growth and Differentiation During Fibroblast Growth Factor–Stimulated Angiogenesis Vitro: Role of Extracellular Matrix," *J. Cell Biol.*, vol. 109, pp. 317–330 (1989).

Jauregui, H.O., et al., "Attachment and Long Term Survival of Adult Rat Hepatocytes in Primary Monolayer Cultures: Comparison of Different Substrata and Tissue Culture Media Formulations," *In Vitro Cellular & Development Biology*, vol. 22, No. 1, pp. 13–22 (Jan. 1986).

Kleinman, H.K., et al., "Use of Extracellular Matrix Components for Cell Culture," *Analytical Biochemistry* 166, 1–13 (1987).

Kolata, Gina, "Parkinson Procedure: Fervor Turns to Disillusion," *The New York Times*, (Apr. 21, 1988).

Kordower, J.H., et al., "An in Vivo and in Vitro Assessment of Differentiated Neuroblastoma Cells as a Source of Donor Tissue for Transplantation," *Annals of the New York Academy of Sciences*, vol. 495, pp. 606–622 (New York 1987).

Kordower, J.H., et al., "Neuroblastoma Cells in Neural Transplants: A Neuroanatomical and Behavioral Analysis," *Brain Research*, 417(1):85–98 (Aug. 4, 1987).

Letourneau, "Possible Roles for Cell–to–Substratum Adhesion in Neuronal Morphogenesis," *Developmental Biology*, 44, 77–91 (1975).

Lewin, "Cloud over Parkinson's Therapy," *Science*, vol. 240, pp. 390–392, (Apr. 22, 1988).

Lewin, "Disappointing Brain Graft Results," *Science*, pp. 1407, (Jun. 10, 1988).

Li, M.L., et al., "Influence of a Reconstituted Basement Membrane and Its Components on Casein Gene Expression and Secretion in Mouse Mammary Epithelial Cells," *Proc. Natl. Acad. Sci. USA* vol. 84, pp. 136–140 (Jan. 1987).

Macklis, J.D., et al., "Cross–Linked Collagen Surface for Cell Culture that is Stable, Uniform, and Optically Superior to Conventional Surfaces," *In Vitro Cellular & Developmental Biology*, vol. 21, No. 3, part 1, pp. 189–194 (Mar. 1985).

Madison, R., et al., "Increased Rate of Peripheral Nerve Regeneration Using Bioresorbable Nerve Guides and a Laminin–Containing Gel," *Exp. Neurol.*, 88(3):767–72 (Jun. 1985).

da Silva, C.F., et al., "An In Vivo Model to Quantify Motor and Sensory Peripheral Nerve Regeneration Using Bioresorbable Nerve Guide Tubes," *Brain Research*, vol. 342, pp. 307–315 (1985).

del Cerro, M., et al., "Retinal Transplants into the Anterior Chamber of the Rat Eye," *Neuroscience* vol. 21(3):707–23 (Jun. 1987).

Doillon, C.J., et al., "Collagen–Based Wound Dressings: Control of the Pore Structure and Morphology," *Journal of Biomedical Materials Research*, vol. 20, pp. 1219–1228 (Oct. 1986).

Doillon, C.J., et al., "Epidermal Cells Cultured on a Collagen–Based Material," G.W. Bailey, Editor, *Proceedinas of the 44th Annual Meeting of the Electron Microscopy Society of America*, (1986).

Folkman, Judah, et al., "Angiogenic Factors," *Science*, vol. 235, pp. 442–447 (Jan. 23, 1987).

Gash, D.M., et al., "Amitotic Neuroblastoma Cells Used for Neural Implants in Monkeys," *Science*, 233(4771):1420–2 (Sep. 26, 1986).

Gash, D.M., "Neural Transplantation: Potential Therapy for Alzheimer's Disease," *J. Neural Transm.*, [Suppl.] 24:301–8 (1987).

Grande, Daniel A., et al., "Healing of Experimentally Produced Lesions in Articular Cartilage Following Chondrocyte Transplantation," *The Anatomical Record* 218:142–148 (1987).

Grande, Daniel A., et al., "The Repair of Experimentally Produced Defects in Rabbit Articular Cartilage by Autologous Chondrocyte Transplantation," (May 11, 1988).

Harris, A.K., et al., "Silicone Rubber Substrata: A New Wrinkle in the Study of Cell Locomotion," *Science* (Wash. D.C.) 208:177–179 (1980).

Henry, E.W., et al., "Nerve Regeneration Through Biodegradable Polyester Tubes," *Exp. Neurol.*, 90(3):652–76 (Dec. 1985).

Ingber, D.E., et al., "Cells as Tensegrity Structures: Architectural Regulation of Histodifferentiation by Physical Forces Transduced Over Basement Membrane," *Gene Expression During Normal and Malignant Differentiation*, L.C. Andersson, et al., editors, pp. 13–32 (Academic Press, Orlando, FL 1985).

Ben–Ze'ev, A., et al., "Cell–Cell and Cell–Matrix Interactions Differentially Regulate the Expression of Hepatic and Cytoskeletal Genes in Primary Cultures of Rat Hepatocytes," *Proc. Natl. Acad. Sci. USA* vol. 85, pp. 2161–2165 (Apr. 1988).

Biers, Elizabeth, "Organogensis' Human Artery Equivalent May Revolutionize Vascular Grafts," *Genetic Engineering News*, (Nov.–Dec. 1987).

Bissell, D. Montgomery, et al., "Interactions of Rat Hepatocytes with Type IV Collagen, Fibronectin and Laminin Matrices, Distinct Matrix–Controlled Modes of Attachment and Spreading," *European Journal of Cell Biology* 40, 72–78 (Mar. 1986).

Bissell, D.M., et al., "Support of Cultured Hepatocytes by a Laminin–Rich Gel, Evidence of a Functionally Significant Subendothelial Matrix in Normal Rat Liver," *J. Clin. Invest.*, vol. 79, pp. 801–812 (Mar. 1987).

Bissell, D.M., et al., "The Role of Extracellular Matrix in Normal Liver," *Scand. J. Gastroenterol.* 23:107 (1988).

Björklund, A., *Annals of the N.Y. Academy of Science*, vol. 495, pp. 676–686 (1987).

Bohn, M.C., et al., "Adrenal Medulla Grafts Enhance Recovery of Striatal Dopaminergic Fibers," *Science* 238(4817):913–6 (Aug. 21, 1987).

"Brain Graft Seeks to Relieve Huntington Disease Patient," *The New York Times*, (Mar. 4, 1988).

Brown, Norman, "Fibrin–Collagen Nerve Repair Device," Inventors: Russ Griffiths, Larry Stensaas and Ken Horch, Letter dated May 10, 1988.

Burke, John F., et al., "Successful Use of a Physiologically Acceptable Artificial Skin in the Treatment of Extensive Burn Injury," *Ann. Surg.*, 194(1):413–428 (1981).

Craig, et al., "A Biologic Comparison of Polyglactin 910 and Polyglycolic Acid Synthetic Absorbable Sutures," *Surgery Gynecology & Obstetrics*, vol. 141, No. 1, pp. 1–10 (Jul. 1975).

Culliton, Barbara J., "Gore Tex Organoids and Genetic Drugs," *Science*, vol. 246. pp. 747–749 (Nov. 1989).

Davis, George E., et al., "Human Amnion Membrane Serves as a Substratum for Growing Axons In Vitro and In Vivo," *Science*, vol. 236, pp. 1106–1109 (May 29, 1987).

Thüroff et al, "Cultured Rabbit Vesical Smooth Muscle Cells for Lining of Dissolvable Synthetic Prosthesis", Urology, V. 21, 155–158, 1983.

Pimpl et al (A), Biological Abstracts 78(4):24889, 1984.

Sasaki et al, Biological Abstracts 82(9):80762, 1986.

Pimpl et al (B) Biological Abstracts 83(8):76014, 1987.

Sapozhnikova et al, Biological Abstracts 86(8):76896, 1988.

Leeson et al Histology WB Saunders Co 1976 pp. 86, 87 and 114.

Structure & Function in Man WB Saunders Co 1982 pp. 85–88, 383, 384, 484 & 413.
Thompson Science 258:744–746 1992.
Culliton Science 246:748 1989.
Kretschmer, et al., *Ann. Surg.* 187, 79–86 (1978).
Naji, et al., *Surgery* 86, 218–226 (1979).
Sutherland, et al., *Surgery* 82, 124–132 (1977).
Groth, et al., *Transplant. Proc.* 9, 313–316 (1977).
Matas, et al., Science 192, 892–894 (1976).
Ebata, et al., *Surg. Forum* 29, 338–340 (1978).
Seldon, et al., *Transplant* 38, 81–83 (1984).
Minato, et al., *Euro. Surg. REs.* 16, 162–169 (1984).
Vroeman, et al., *Transplantation* 42, 130–135 (1986).
Strom, et al., *JNCI* 68, 771–778 (1982).
Vacant, et al J Pediatric Surgery 23(1) 3–9 1982.
Leong, et al J Biomedical Materials Research vol. 19:941–955 1985.

IMPLANTATION OF CELL-MATRIX STRUCTURE ADJACENT MESENTERY, OMENTUM OR PERITONEUM TISSUE

This application is a continuation of application Ser. No. 07/680,608, filed Apr. 1, 1991, now abandoned, which is a continuation of application Ser. No. 07/343,158, filed Apr. 25, 1989, now abandoned, which is a continuation of application Ser. No. 07/123,579, filed Nov. 20, 1987, now abandoned, which is a continuation-in-part of application Ser. No. 06/933,018, filed Nov. 20, 1986, now abandoned.

BACKGROUND OF THE INVENTION

This invention generally relates to organ implantation and more specifically is a method for implanting large volumes of cells on polymeric matrices into a patient.

There are many diseases which cause significant scarring of the liver, ultimately causing hepatic failure. There are no artificial support systems for liver failure, so that, in the absence of a successful transplant, liver failure always results in the death of the patient. It has been estimated that 30,000 people die of hepatic failure every year in the United States, at a cost to society of $14 billion dollars annually. Some of these diseases include genetic defects that result in defects of protein metabolism, defects of amino acid metabolism, defects of carbohydrate metabolism, defects of pyrimidine and purine metabolism, defects of lipid metabolism, and defects of mineral metabolism. Another group of patients suffering from liver disease are those with alcohol induced liver disease. At this time, these patients have no options.

Over the last few years, organ implantation has become an increasingly important method for treating organ dysfunction. Unfortunately, despite the current success in transplantation of a variety of organs, especially the liver, many people die as a result of the critical shortage of donor organs. The only method for treating those patients for which transplantation is an option is to maintain them until a liver becomes available for transplantation.

Transplantation of the whole liver has become an increasingly successful surgical manipulation through the 1980's, largely through the efforts of Dr. Thomas Starzl. However, the technical complexity of the surgery, the enormous loss of blood, the stormy postoperative course, and the many unknowns of hepatic transplantation, have made it an expensive technology available only in major medical centers. It has become increasingly clear that because of donor scarcity, transplantation will never meet the needs of the patients who require it. Currently, approximately 1500 patients per year undergo hepatic transplantation. Even if that capacity were tripled, it would fall short of the 30,000 patients dying of end-stage liver disease.

The emergence of organ transplantation and the science of immunobiology has allowed replacement of the kidney, heart, liver, and other organs. However, as the ability to perform these complex operations has improved, the limitations of the technology have become more evident. The surgery is complex and usually associated with major blood loss. The preservation time is short and, therefore, results in major logistical problems in matching a distant donor with a recipient. For these reasons, the undertaking is expensive and labor intensive, requiring a major investment of resources available only in tertiary care facilities.

Selective cell transplantation of only those parenchymal elements necessary to replace lost function has been proposed as an alternative to whole or partial organ transplantation. This has several attractive features, including avoiding major surgery with its attendant blood loss, anesthetic difficulties, and complications. It replaces only those cells which supply the needed function and, therefore, problems with passenger leukocytes, antigen presenting cells, and other cell types which may promote the rejection process are avoided. Adding the techniques of cell culture provides another set of tools to aid in the transplantation process. The ability to expand cell numbers with proliferation of cells in culture, in theory, allows autotransplantation of one's own tissue.

Recently, a number of groups have engaged in research and development of various ways to grow cells in vitro for subsequent implantation, as well as to directly implant the cells in vivo. Most such efforts have met with only limited success due to problems with the cells failing to proliferate and function once implanted.

W087/06120 by Marrow-Tech Incorporated describes successfully growing in vitro cells such as bone marrow cells on nylon meshes seeded with stromal cells. A.A.Demetriou,et al., *Science* 233,1190–1192 (1986) describes implantation and function of hepatocytes attached to collagen coated microcarrier beads injected into the peritoneal cavity. Others have directly implanted in vivo pancreatic tissue into diabetic patients. An earlier approach which was not successful in achieving long-term benefits was the transplantation of islet cells through injection of isolated clusters of islet cells into the portal circulation, with implantation in the vascular bed of the liver. More recent experimental methods have included encapsulation of pancreatic beta cells to prevent immune attack by the host and injection of fetal beta cells beneath the capsule of the kidney. Although there is evidence of short term function, long term results have been less satisfactory (D. E. R. Sutherland, *Diabetologia* 20, 161–185 (1981) ; D. E. R. Sutherland, *Diabetologia* 20,435–500 (1981)), and whole organ pancreatic transplantation has remained the preferred treatment.

In U.S. Ser. No. 123,579 entitled "Chimeric Neomorphogenesis of organs by Controlled Cellular Implantation Using Artificial Matrices" filed Nov. 20, 1987 by Joseph P. Vacanti and Robert S. Langer, and U.S. Ser. No. 933,018 entitled "Chimeric Neomorphogenesis of Organs Using Artificial Matrices" filed Nov. 20, 1986 by Joseph P. Vacanti, a method and matrices were disclosed that allow cells of a variety of types to be proliferated in vitro prior to implantation in vivo and vascularization. The principal element of both the method and the matrices is that the three dimensional support structure provides sufficient spacing between seeded cells for adequate diffusion of nutrients and gas exchange from the surrounding media to occur in the absence of vascularization.

However, even this method and matrices still require implantation of the proliferating cell mass, especially of cells such as hepatocytes, pancreas, and other endocrine cells, into the patient using surgical procedures creating a wound which can then produce inflammation and hematoma formation. Further, it requires implantation of a large volume of cells for the cells to proliferate and function.

It is therefore an object of the present invention to disclose a method and means for implanting large volumes of cells to form a variety of organs, especially endocrine organs including liver, pancreas and adrenal gland, which functionally resemble the naturally occurring organs.

It is a further object of the present invention to provide a method for implanting large volumes of cells on biodegradable, non-toxic matrices to form functional organ equivalents which is relatively non-invasive and traumatic as compared to conventional surgical procedures.

SUMMARY OF THE INVENTION

The present invention is a method and means whereby large volumes of cells having a desired function are attached to polymer scaffolding and transferred with minimal wounding and blood loss into a patient at a site appropriate for attachment, growth and function of the cells on the scaffolding, thereby producing a functional organ equivalent. The method involves seeding cells onto a number of matrices, then implanting the matrices in vivo between tissues so that the implanted cells are provided with adequate nutrition and gas exchange, even in the absence of vascularization, but in volumes sufficiently large to provide the required function. The method is particularly well suited for growth of endocrine structures, including liver, pancreas, and adrenal gland, but can be used for growth and function of other types of tissue.

In the preferred embodiment, seeded polymer sheets are placed between folds of the mesentery. The vascular supply from the portal circulation supplies nutrients and normal metabolic factors to the implanted cells by diffusion until ingrowth of blood vessels following implantation provides for normal feedback mechanisms controlling the soluble products of the implanted cells. The preferred material for forming the matrix or support structure is a biodegradable artificial polymer, for example, polyglycolic acid, polyorthoester, or polyanhydride, which is degraded by hydrolysis at a controlled rate and reabsorbed. These materials provide the maximum control of degradability, manageability, size and configuration. Further, materials such as angiogenesis factors can be incorporated into degradable matrices for use in preparing the implantation sites prior to, or at the time of, implanting the cells.

Initially growing the cells in culture allows manipulation and proliferation of the cells which may be beneficial following implantation of the matrix cell structures, but is not required if adequate cells for seeding can be obtained by biopsy.

BRIEF DESCRIPTION OF THE DRAWINGS

FIG. 1A is a side view and FIG. 1B is frontal view.

DETAILED DESCRIPTION OF THE INVENTION

A method allowing large volumes of unvasculated cells to be simultaneously implanted in a patient with minimal wounding is based on the discovery that multiple seeded polymeric matrices can be juxtaposed with certain tissues and undergo adequate exchange of nutrients and gases to grow and proliferate. These tissues, such as the mesentery and the omentum, have large surface areas and are highly vasculated.

The peritoneum is an extensive serous membrane lining the abdominal cavity and many of the organs in the cavity. The "mesentery" is ordinarily used to refer to the mesentery of the small intestine, a double-layered fold of peritoneum suspending it from the posterior abdominal wall. The attached border of the mesentery is only about 15 cm in length, and runs from approximately the second lumbar vertebra downward and to the right, crossing part of the duodenum, the aorta, the inferior vena cava, and across towards the right sacroiliac joint. The free or unattached border, containing the jejuno-ileum, is frilled out like an accordion, attaining a length ranging from three to six meters. The distance from the free border to the attached border ranges from 15 to 22 cm in length.

Figure 1A:
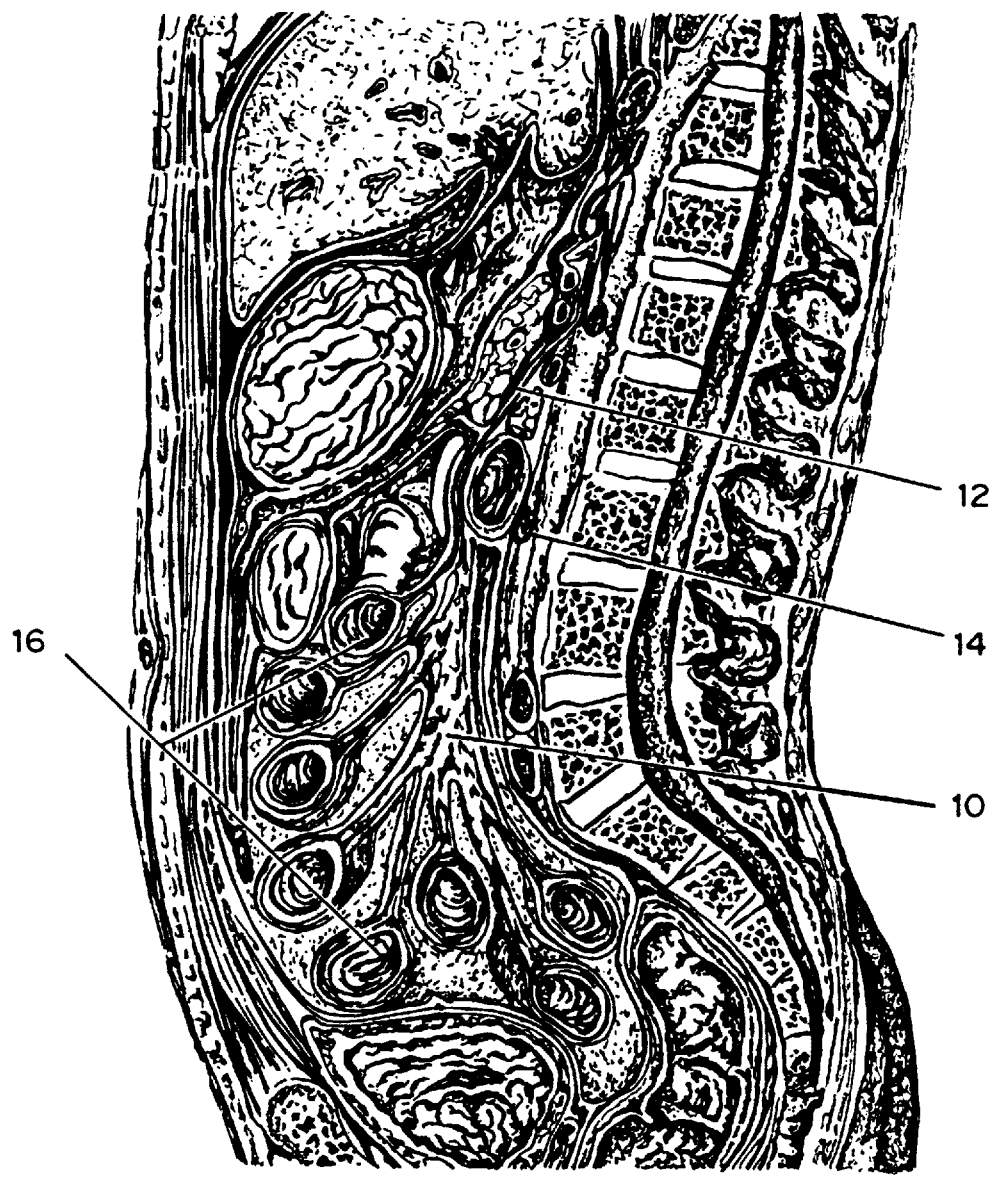
FIG. 1A and 1B are saggital sectional views of an adult human showing the various elements of the upper and lower gastrointestinal tract, including the small intestines and the mesentery.
Figure 1B:
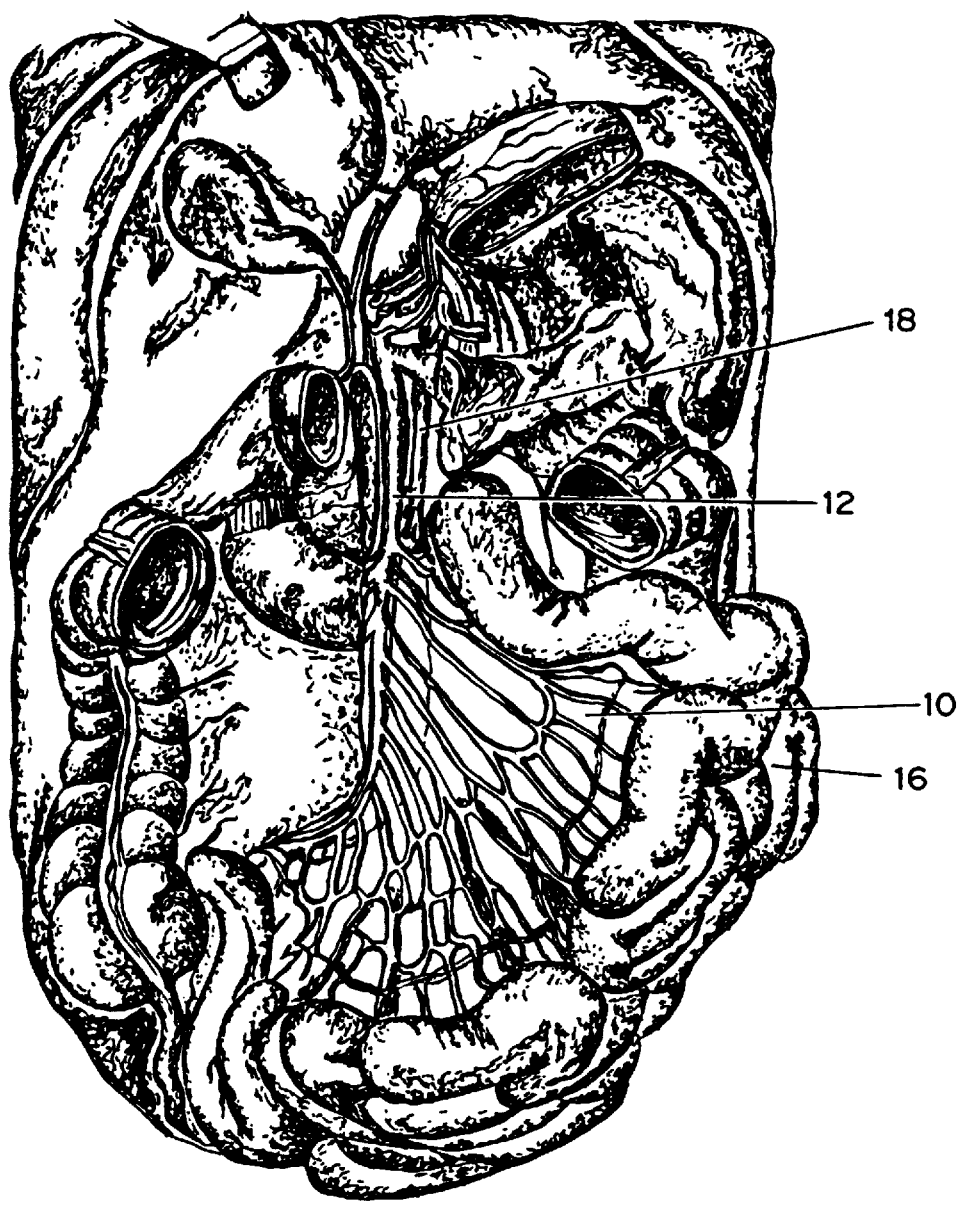
Figure 2:
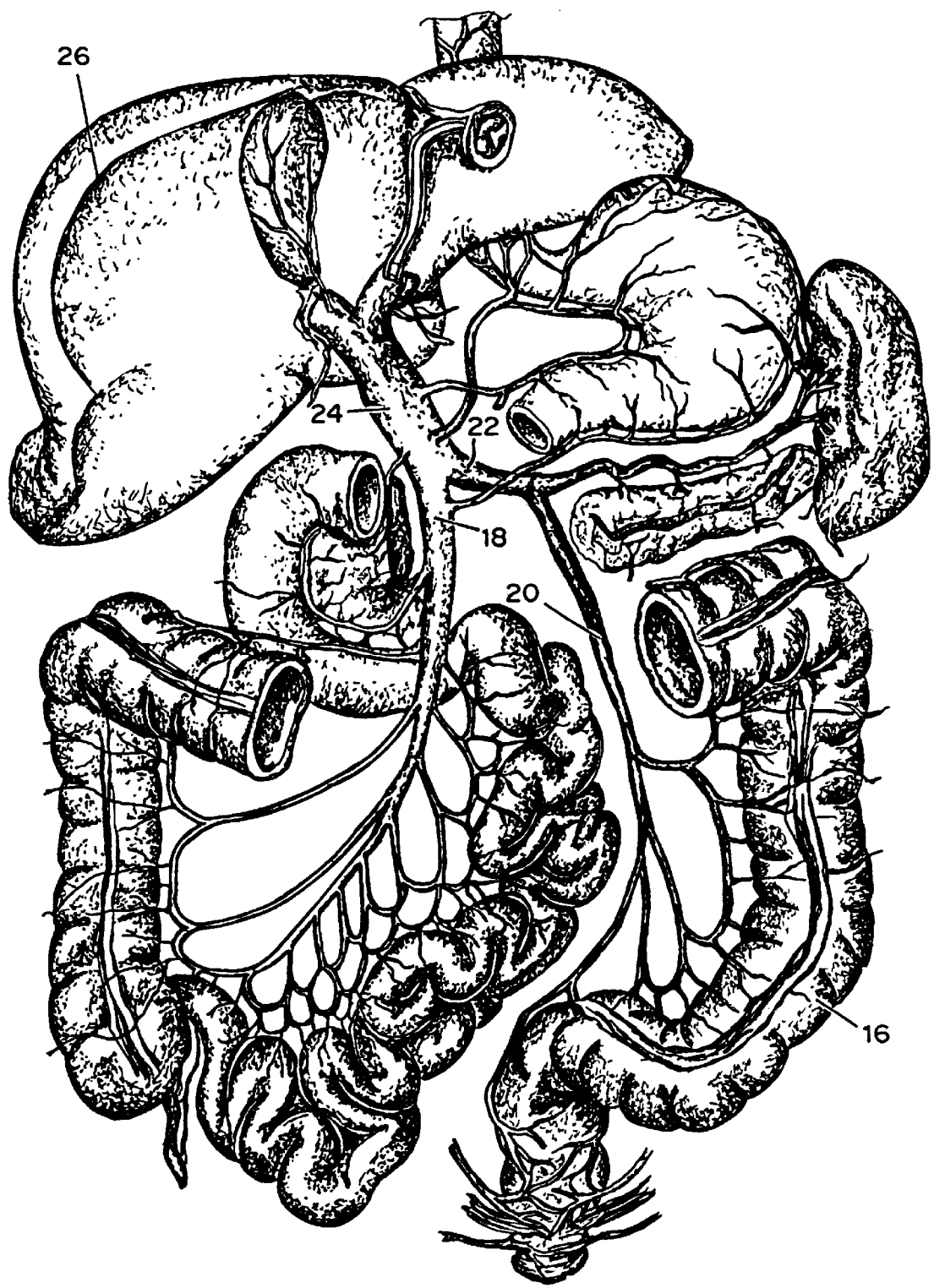
FIG. 2 is a view of the veins of the circulatory system associated with the mesentery.

Between the two layers of peritoneum, on the two surfaces of the mesentery, are the superior mesenteric artery and its branches, the accompanying veins, lymphatics, lymph nodes, connective tissue, and varying amounts of adipose tissue. The mesentery is shown in cross section in FIGS. 1A and 1B. With reference to FIG. 1A, the mesentery 10 is connected to the superior 12 and inferior 14 mesenteric arteries, supplying blood to the small intestine 16. With reference to FIG. 1B, the mesentery 10 expands outwardly like a fan to the small intestine 16, the superior mesenteric artery 12 draining into the superior mesenteric vein 18. As shown in FIG. 2, the inferior mesenteric vein 20 drains blood from the splenic 22, coronary and pyloric veins. The superior mesenteric vein 18 drains into the portal vein, leading to the liver 26. The vascular supply from the portal circulation supplies nutrients and normal metabolic factors to the implanted cells by diffusion until ingrowth of blood vessels following implantation provides for normal feedback mechanisms controlling the soluble products of the implanted cells.

The omentum is a double fold of peritoneum attached to the stomach and connecting it with some of the other organs, including the intestines. Other sections of the peritoneum and isolated tissues having similar characteristics can also be used in the method for implanting large volumes of cells.

Figure 3:
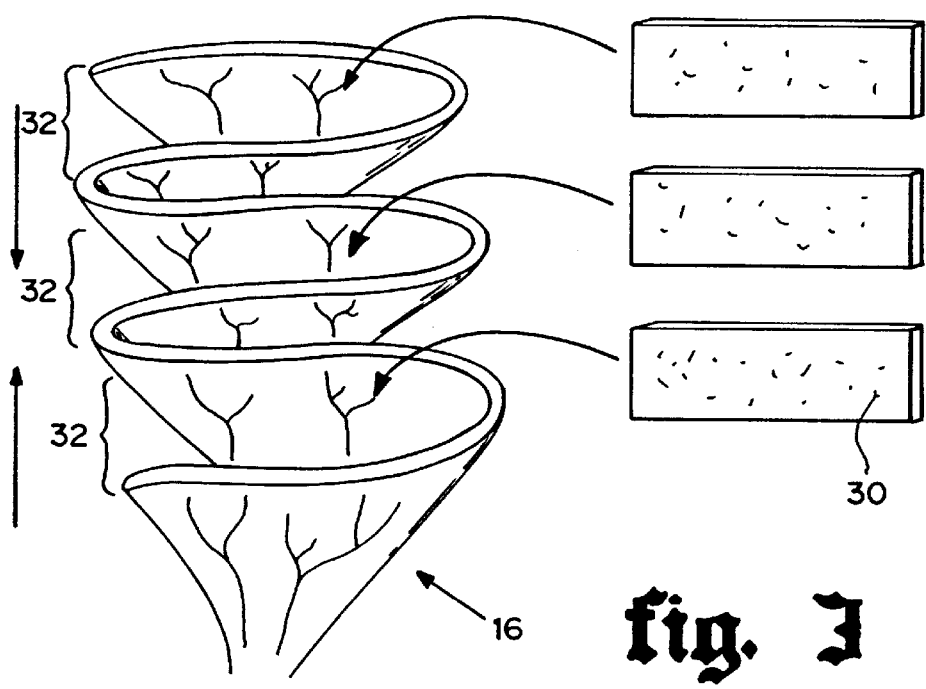
FIG. 3 is a diagram of the method of the present invention showing implantation of polymer sheets seeded with cells being placed between folds of the mesentery according to the method of the present invention.
Figure 3:
Figure 4:
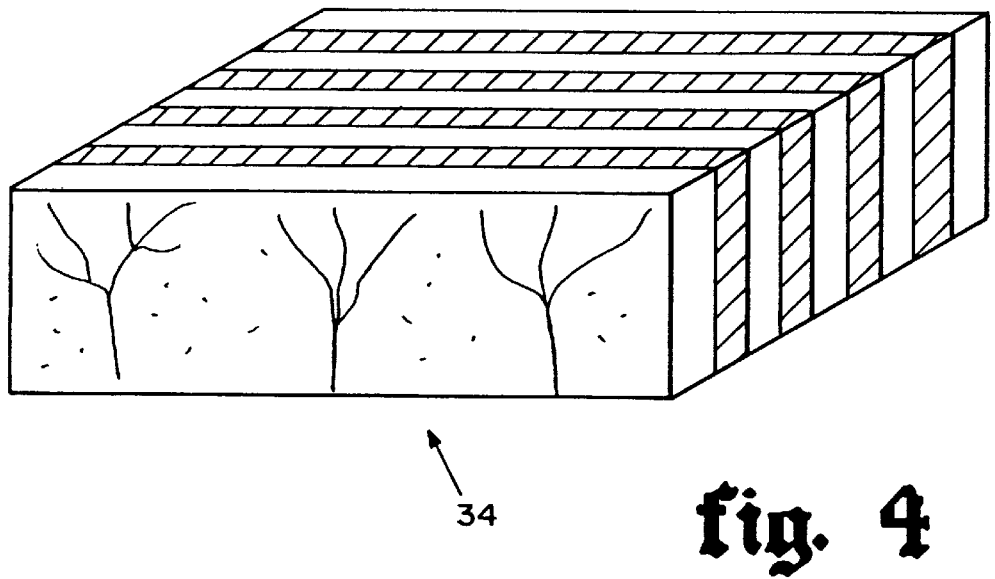
FIG. 4 is a diagram of the chimeric structure resulting from the insertion of the polymer sheets, as shown in FIG. 3, loosely approximated together to form a chimeric cell matrix structure according to the present invention.

As shown schematically in FIGS. 3 and 4, chimeric cell-polymeric structures are formed by seeding biodegradable, biocompatible high surface area matrices with cells, derived from biopsy of the patient or a close relative or from cell culture, and implanting the seeded matrices 30 between folds 32 of the mesentery 16. The folds 32 of the mesentery are approximated together to form a chimeric structure 34.

The preferred material for forming the matrix or support structure is a biodegradable artificial polymer, for example, polylactic acid, polyglycolic acid, polyorthoester, polyanhydride, or combination thereof, which is degraded by hydrolysis at a controlled rate and reabsorbed. These materials provide the maximum control of degradability, manageability, size and configuration. However, other biocompatible polymeric materials, including collagen and non-biodegradable materials, can be used to form the structures. In some embodiments these materials are overlaid with a second material such as basement membrane components, agar, agarose, gelatin, gum arabic, collagens, fibronectin, laminin, glycosaminoglycans, mixtures thereof, and other materials having properties similar to biological matrix molecules known to those skilled in the art of cell culture to enhance cell attachment.

The major advantage of the biodegradable material is that it does not have to be removed once cell growth and formation of a functional mass has occurred. Another advantage of the biodegradable material is that compounds may be incorporated into the matrix for slow release during degradation of the matrix. For example, angiogenic compounds, nutrients, growth factors, inducers of differentiation or de-differentiation, products of secretion, immunomodulators, inhibitors of inflammation, regression factors, biologically active compounds which enhance or allow ingrowth of the lymphatic network or nerve fibers, and drugs can be incorporated into the matrix or provided in conjunction with the matrix, in solution or incorporated into a second biodegradable polymer matrix.

In another embodiment of the invention, a matrix containing one or more of these biologically active compounds is implanted in the tissue prior to implantation of seeded matrices, to prepare the implantation site, for example, using angiogenic compounds to pre-vascularize the site.

In the preferred embodiment, multiple polymeric matrices formed of fibrous sheets are inserted into either a fresh bed or a prevascularized bed in the mesentery to create a structure having overall dimensions between a few microns to several centimeters. Matrices can be made in a variety of shapes, taking into consideration the requirements of adequate surface area for attachment of the number of cells required for implantation and formation of a function organ equivalent, and the requirements of adequate spacing between surfaces of attachment for nutrients and gases to diffuse into the interior of the matrices to each attached cell. The latter requirement can be met by providing many relatively thin matrices and implanting each sheet between folds of the mesentery, or by providing matrices having overall dimensions greater than the maximum diffusion distance for nutrients into an equal volume of cells, as described in U.S. Ser. No. 123,579 entitled "Chimeric Neomorphogenesis of Organs by Controlled Cellular Implantation Using Artificial Matrices" filed Nov. 20, 1987 by Joseph P. Vacanti and Robert S. Langer, and U.S. Ser. No. 933,018 entitled "Chimeric Neomorphogenesis of Organs Using Artificial Matrices" filed Nov. 20, 1986 by Joseph P. Vacanti, the teachings of which are incorporated herein.

A variety of different cells can be seeded onto the matrix. In the preferred embodiment, endocrine cells such as hepatocytes, pancreatic cells or cells of the adrenal gland are proliferated on the matrices. Other cells, such as cells of the nervous system, including hypothalamus and pituitary cells, lymphoid cells, mesodermal cells, such as fibroblasts, endothelial cells, and lymphatic cells, splenic cells, and genitourinary cells, for example, renal endocrine tissues, and sex related endocrine tissues, can also be implanted using this method.

With respect to the endocrine cells, where the cells are positioned on multiple matrices within the mesentery, the method locates these cells within the blood stream in close proximity to the blood supply the organs normally receive, between the portal and systemic systems. This exposes the cells to many of the factors present in the blood that aid in normal growth and proliferation.

Cells of one or more types can be selected and grown on the matrix. The matrix structure and the length of time and conditions under which the cells are cultured in vitro are determined on an individual basis for each type of cell by measuring cell attachment (only viable cells remain attached to the polymers), extent of proliferation, and percent successful engraftment. As discussed above, it is not necessary to culture cells in vitro, other than for purposes of attaching the cells to the matrix, prior to implantation if sufficient numbers of cells are available. Cells generally attach within a few hours.

Initially growing the cells in culture allows manipulation of the cells which may be beneficial following implantation of the matrix cell structure. Presently available technology allows the introduction of genes into the cells to make proteins which would otherwise be absent, such as those resulting from liver protein deficiencies and metabolic defects such as cystic fibrosis. Repression of gene expression may also be used to modify antigen expression on the cell surface, and thereby the immune response, so that cells are not recognized as foreign. obtained by biopsy.

The present invention will be further understood by reference to the following non-limiting example.

Hepatocytes were obtained from Fischer 34 and Gunn rats by collagenase perfusion. Cells were seeded onto non-woven filamentous sheets of polyglycolic acid 1×3 cm in size and 2 mm thick to a density of 500,000 cells/cm$^2$. Recipient animals underwent laparotomy using sterile technique and sheets were placed between leaves of mesentery. Eight sheets were placed per animal and the leaves were approximated, creating a functional implant 1×1×3 cm.

Biopsy at day five post implantation revealed neovascularization, moderate inflammatory reaction, and the presence of viable hepatocytes.

This example demonstrates the successful implantation of large volumes of hepatocytes, cells which do not normally remain viable in the absence of a polymeric support, and which are difficult to proliferate in vivo to a number sufficient to form a functional organ equivalent, using multiple polymeric sheets placed into folds of the mesentery, with minimal trauma and blood loss.

Modifications and variations of the present invention, a method for implanting large volumes of functional cells on polymeric matrices in vivo, and the product thereof, will be obvious to those skilled in the art from the foregoing detailed description of the invention. These modifications and variations are intended to come within the scope of the appended claims.

We claim:

1. A method of implanting a matrix structure having cells attached thereto comprising
   a) providing a biocompatible polymeric matrix structure having attached thereto viable animal cells exhibiting normal growth and proliferation selected from the group consisting of endocrine cells, fibroblasts, endothelial cells, and genitourinary cells, which are allowed to attach thereto; and
   b) implanting the matrix structure having cells attached thereto into a patient in need thereof, wherein the matrix structure is juxtaposed with tissue having high surface area and vasculature; adjacent the surface of the tissue selected from the group consisting of mesentery, omentum and peritoneum, and wherein the matrix structure is configured to allow adequate nutrients and gas exchange between the attached cells and the blood for the cells to remain viable and to form tissue.

2. The method of claim 1 wherein the tissue is the mesentery.

3. The method of claim 1 wherein the tissue is the omentum.

4. The method of claim 1 wherein the tissue is the peritoneum.

5. The method of claim 1 wherein the matrix is formed of a polymer selected from the group consisting of polylactic acid, polyglycolic acid, polyorthoester, polyanhydride, and combinations thereof.

6. The method of claim 1 wherein the cells are endocrine cells selected from the group consisting of hepatocytes, pancreatic cells, and adrenal cells.

7. The method of claim 1 further comprising incorporating into the matrix structure a compound selected from the group consisting of angiogenic compounds, protein growth factors, and immunomodulators.

8. The method of claim 1 comprising implanting prior to implantation of the matrix structure with attached cells a matrix containing a compound selected from the group consisting of angiogenic compounds, protein growth factors, and immunomodulators.

9. The method of claim 1 comprising culturing the viable cells attached to the polymeric matrix structure in vitro prior to implanting the matrix structure having cells attached thereto in vivo.

10. The method of claim 1 further comprising introducing a gene into the cells prior to attachment to the matrix structure to alter expression of a gene encoding a protein.

11. The method of claim 1 wherein multiple matrix structures having cells attached thereto are implanted which functionally resemble naturally occurring organs.

12. The method of claim 11 wherein matrix structures with one type of cell attached thereon are implanted in juxtaposition with matrix structures having other types of cells attached thereon.

13. The method of claim 1 wherein the matrix structure is formed of collagen.

14. The method of claim 1 wherein the matrix structure is formed of a non-biodegradable, biocompatible polymer.

* * * * *

UNITED STATES PATENT AND TRADEMARK OFFICE
CERTIFICATE OF CORRECTION

PATENT NO. 5,804,178
DATED     September 8, 1998
INVENTORS Joseph P. Vacanti, Robert S. Langer, and Lynt Johnson It is certified that error appears in the above-identified patent and that said Letters Patent is hereby corrected as shown below:

Item [56] References Cited:
Page 2, under U.S. Patent Documents:
    Line 4,888,178 replace "Larger" with --Langer--;

Page 2, under Other Publications:
    Column 1, line Allcock, H.R., et al., replace "Phosponitrillic" with --Phosphonitrilic--;

Page 2, under Other Publications:
    Column 2, line Rosen, Howard B., et al., replace "Bloerodible" with --Bioerodible--;

Page 4,
    Column 1, line Doillon, C.J., et al, replace "*Proceedinas*" with --*Proceedings*--.

Signed and Sealed this

Tenth Day of April, 2001

Attest:

NICHOLAS P. GODICI

Attesting Officer    *Acting Director of the United States Patent and Trademark Office*